United States Patent [19]
Weadock

[11] Patent Number: 6,110,184
[45] Date of Patent: Aug. 29, 2000

[54] INTRODUCER WITH VASCULAR SEALING MECHANISM

[76] Inventor: Kevin S. Weadock, 1 Koster Ct., Huntington, N.Y. 11746

[21] Appl. No.: 09/366,900

[22] Filed: Aug. 4, 1999

[51] Int. Cl.[7] ................................................ A61B 17/04
[52] U.S. Cl. ........................................ 606/144; 148/213
[58] Field of Search .................................. 606/139, 144, 606/145, 147, 148, 213

[56] References Cited

U.S. PATENT DOCUMENTS

| | | | |
|---|---|---|---|
| 5,192,300 | 3/1993 | Fowler | 606/213 |
| 5,324,306 | 6/1994 | Makower et al. | 606/213 |
| 5,354,271 | 10/1994 | Voda | 604/49 |
| 5,441,517 | 8/1995 | Kensey et al. | 606/213 |
| 5,522,840 | 6/1996 | Krajicek | 606/213 |
| 5,741,223 | 4/1998 | Janzen et al. | 604/15 |
| 5,792,152 | 8/1998 | Klein et al. | 606/144 |
| 5,868,778 | 2/1999 | Gershony et al. | 606/194 |
| 5,906,631 | 5/1999 | Imran | 606/213 |
| 5,984,948 | 11/1999 | Hasson | 606/213 |
| 6,017,359 | 1/2000 | Gershony et al. | 606/213 |

*Primary Examiner*—Gary Jackson
*Attorney, Agent, or Firm*—Mathews, Collins, Shepherd & Gould, P.A.

[57] ABSTRACT

An introducer for use in interventional vascular procedures having a sealing mechanism for closure of a puncture site is disclosed. The introducer has a vessel-engaging component and a sealing component thereon. The vessel-engaging component comprises an elongated filament engaged within a channel in the wall of the introducer. The filament has an expandable part that is changeable from a first configuration to a second, expanded configuration. When the distal end of the introducer is inserted into the lumen of a blood vessel, the expandable part may be inflated. Pulling the introducer through the puncture in a direction opposite the vessel then causes the expandable member to be engaged on the vessel wall at the location of the puncture to provide resistance in pulling the introducer away from the blood vessel. In this way, the vessel-engaging component locates the puncture site. The sealing component comprises an applicator and a plurality of rings comprised of thrombogenic materials such as collagen on the wall of the introducer. The applicator is used to position the rings at the puncture site once it is located with the vessel-engaging component.

16 Claims, 10 Drawing Sheets

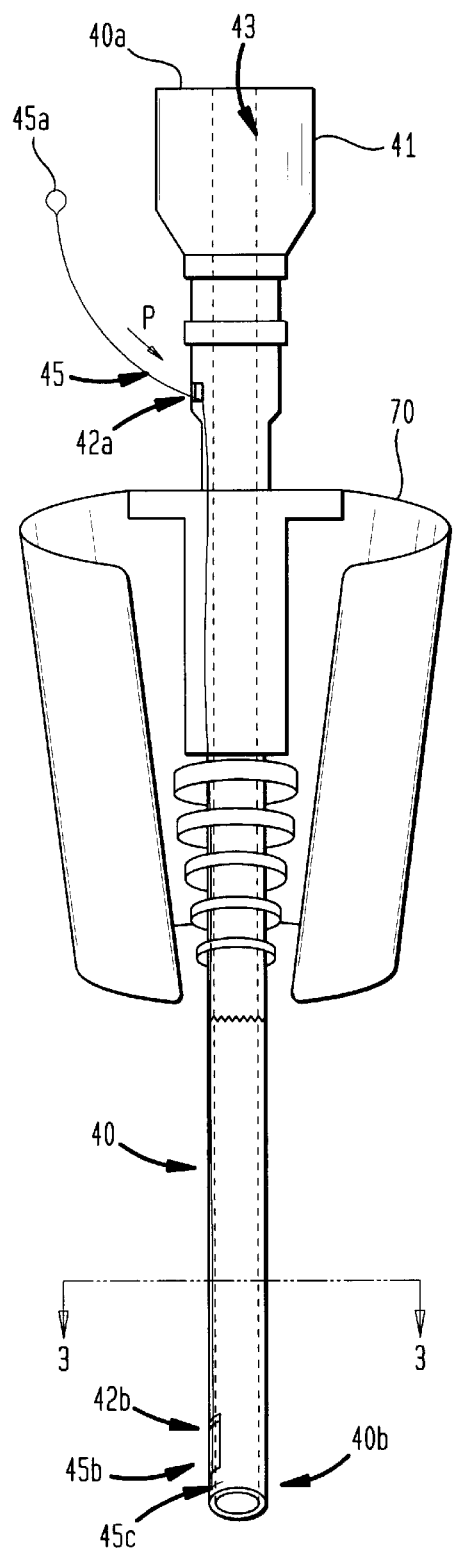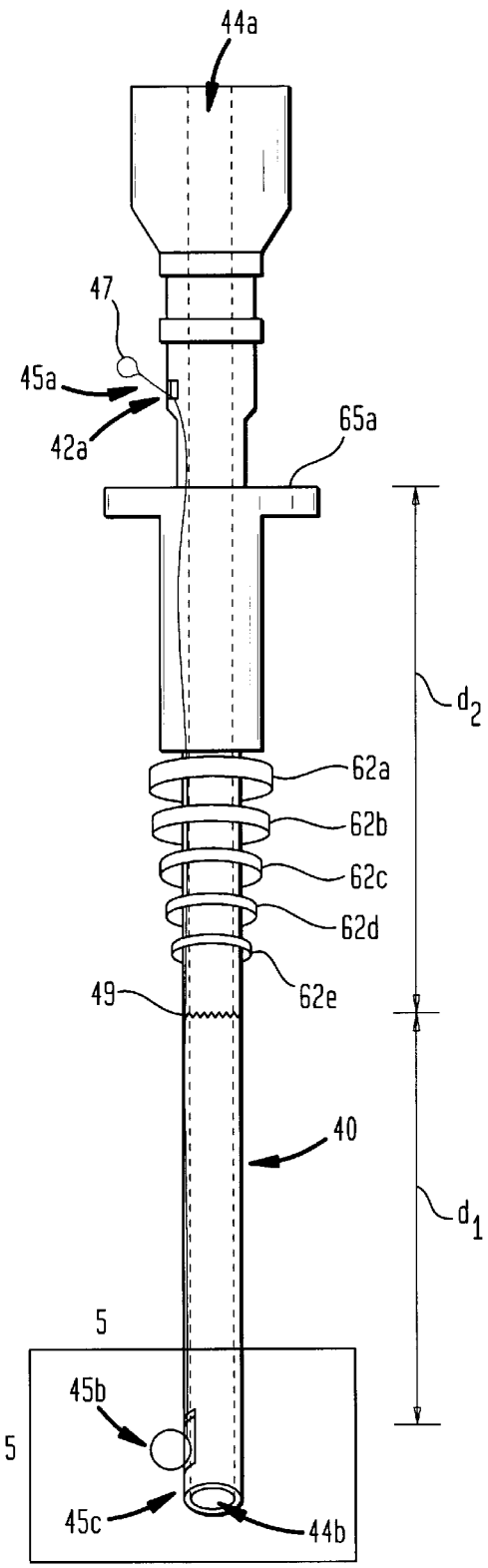

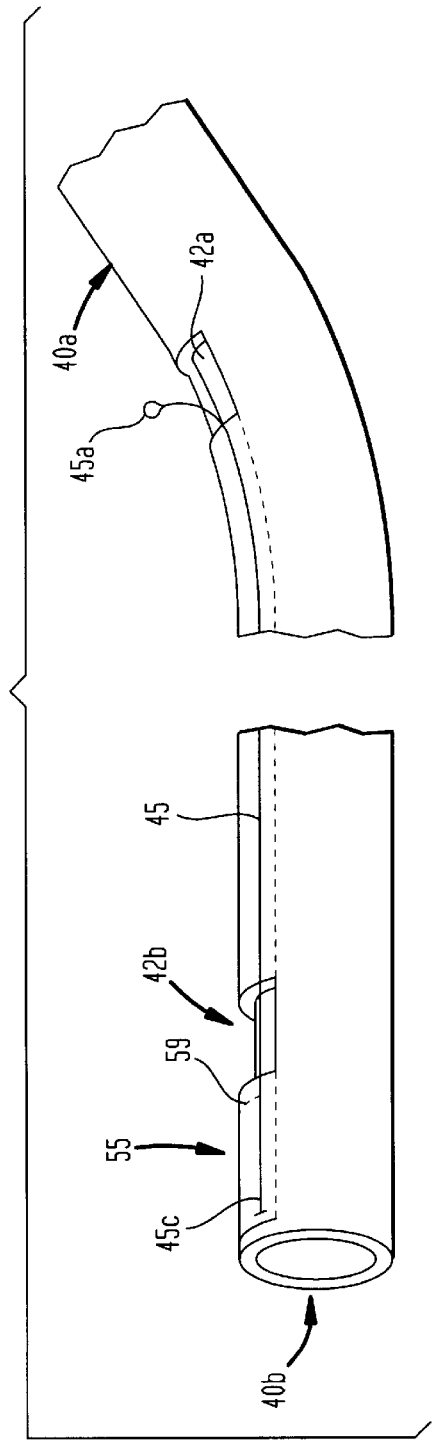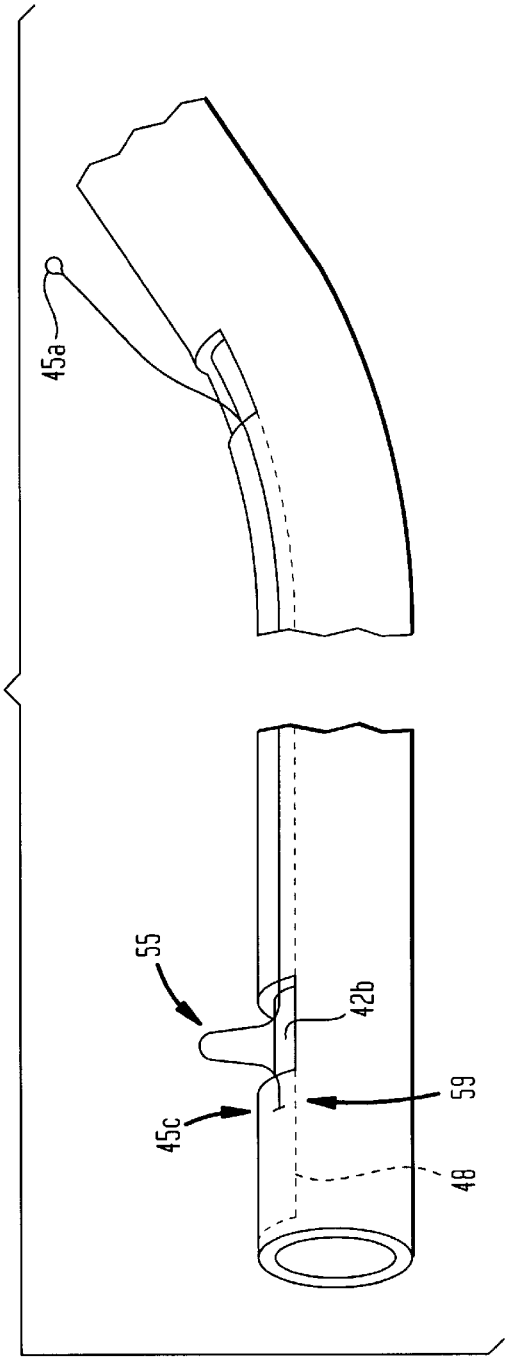

INTRODUCER WITH VASCULAR SEALING MECHANISM

FIELD OF THE INVENTION

The present invention relates to an introducer for use in interventional vascular procedures and, more particularly, to an introducer having an integral sealing mechanism for closure of a puncture site in a blood vessel.

BACKGROUND OF THE INVENTION

In certain medical procedures including interventional procedures such as angioplasty, angiography, and stenting, it often is necessary that an artery be punctured to gain access to the site needed to be diagnosed or treated, typically the region of the heart. The process of inserting the catheter in a proper position within the arterial lumen typically requires that many steps be performed involving inserting and removing various devices into the artery. At the end of the process, the devices are removed leaving a hole in the arterial wall that must be sealed, preferably as soon as possible. Failure to achieve hemostasis at the puncture site may lead to serious bleeding consequences, especially if the patient has been treated with anticoagulants, which often is the case with patients subjected to these procedures.

The artery most often used for this purpose is the femoral artery as it is relatively large and easy to locate. The femoral artery is punctured and a catheter is inserted into the lumen thereof to gain access to the site of concern. Access to the femoral artery is typically gained at the groin area. The femoral artery is easily located here, and the arterial wall is punctured with a needle. In a typical Seldinger technique, a guide wire is inserted through the needle into the lumen of the artery (the needle is hollow for this purpose). Once the guide wire is in place, the needle is removed. A procedural sheath or "introducer," and often a dilator within the introducer, are then both passed over the guide wire and inserted into the arterial lumen. The instrument used at this step of the process is referred to herein as the "introducer," as it is used to introduce procedural catheters, guiding catheters or other medical devices in the arterial lumen. The term "procedural sheath" is also used in the field to refer to the introducer device, and these terms are considered herein to be interchangeable. Once the introducer is in place, the guide wire and dilator may be removed. The catheter is fed through the introducer into the arterial lumen. As a result of these procedures, the practitioner can be assured that the catheter is properly positioned in the lumen of the artery.

This process is now explained more specifically with reference to FIG. 1. In FIG. 1, there is illustrated a typical introducer 10 which is shown lodged within the arterial lumen 12. The introducer 10 has a distal end or tip 101 inserted into the lumen, and a proximal end 102 protruding in the ambient beyond the surface 19 of the patient's skin. As can be seen, the distal end of the introducer adjacent the tip 101 is flexible so that it may bend within the lumen. In FIG. 1, a needle is used to puncture the skin surface 19, layers of fat tissue 16, and the arterial wall 18 forming a wound tract 20*a* through the patient's tissues and a puncture site 20 on the arterial wall. The process of inserting the introducer 10 through the puncture site 20 is performed as described above using a guide wire and dilator (not shown in FIG. 1). In FIG. 1, the catheter 30 has been inserted through the introducer with its distal end 30*a* protruding into the lumen beyond the tip 101 of the introducer and its proximal end 30*b* protruding into the ambient beyond the proximal end 102 of the introducer. As may be seen, the introducer thus enables the practitioner to properly position within the arterial lumen guiding catheters, procedural catheters, and other medical devices to effect treatment of the patient.

However, when the procedure is completed, the catheter and introducer need to be removed and the puncture site closed. Conventional treatment has been to remove these devices and then apply pressure, e.g., "manual compression," to the artery for a period of about twenty minutes to one-half hour or longer to induce hemostasis. This procedure typically requires a clamp or sand-bags and the attention of health-care professionals. Also, the patient is required to remain immobilized in a horizontal position for many hours, sometimes up to 24 hours, with sand-bags placed on the area of the puncture, i.e., the groin area. This is painful and uncomfortable for the patient and is inefficient in consuming resources of the health-care facility. Additionally, the wounds thus sealed often are prone to reopen, and this contingency requires additional monitoring by the health-care professionals and causes anxiety to the patient.

Recently, many efforts have been directed toward developing devices that may be used to better close the puncture site. For example, devices developed to accomplish this objective are disclosed in the following patents which are incorporated herein by reference: U.S. Pat. No. 5,741,223 issued Apr. 21, 1998 to Janzen et al., "Device and Method for Sealing Puncture Wounds" ("Janzen"); U.S. Pat. No. 5,354,271 issued Oct. 11, 1994 to Voda, "Vascular Sheath" ("Voda"); U.S. Pat. No. 5,441,517 issued Aug. 15, 1995 to Kensey et al., "Hemostatic Puncture Closure System and Method of Use" ("Kensey"); U.S. Pat. No. 5,324,306 issued Jun. 28, 1994 to Makower et al., "Hemostatic Implant Introducer" ("Makower"); U.S. Pat. No. 5,868,778 issued Feb. 9, 1999 to Gershony et al., "Vascular SealingApparatus and Method," and U.S. Pat. No. 5,792,152 issued Aug. 11, 1998 to Klein et al., "Device and Method for Suturing of Internal Puncture Sites." Objectives with these devices include reducing the morbidity of the procedure, enabling the patient to leave the hospital sooner, increasing the number of patients that can be treated daily, and reducing the amount of pain, discomfort, and distress endured by the patients. These devices employ sutures to close the artery or a variety of other means to deliver thrombogenic materials such as collagen to the outside of the artery. With these devices, a special additional applicator is typically used, either with or without the introducer, to deliver the thrombogenic materials to the puncture site.

For example, Janzen describes an apparatus for insertion of collagen to the puncture site. The Janzen device includes a dedicated sheath (e.g., an additional sheath besides the introducer), a collagen cartridge, and a collagen pusher. With this device, the introducer (10, FIG. 1) (referred to in Janzen as the "guide cannula"), is first removed with the guide wire left in place in the arterial lumen. The dedicated applicator of Janzen is then passed over the guide wire to the puncture site. With the Janzen device, the introducer is removed before closure is effected presenting the risk of bleeding at the puncture site. To avoid the risk that collagen will enter the arterial lumen, Janzen recommends that the end of the collagen applicator be larger than the arterial puncture. Also, Janzen requires an additional measuring step with use of a clamp and/or a kit of sheaths of varying lengths to measure arterial depth and locate the arterial puncture site (e.g., Janzen, col. 8, lines 38–55).

Voda shows a device referred to therein as a "carrier means" having suture threads located on its end (e.g., FIGS.

8–11 of Voda). The device of Voda provides advantages as compared with that of Janzen as closure of the puncture site is attempted without removal of the introducer, thus reducing risks associated with immediate bleeding at the puncture site. However, Voda requires an additional "carrier means" device. The carrier means is inserted into the introducer, and suture threads are then used to pull the puncture site closed. Closure of the puncture site with suture threads in this way may present considerable challenges to the practitioner. The Klein and Andreas patents likewise disclose devices for suturing the puncture site.

Kensey shows a device for delivery of collagen to the puncture site and puncture tract. Again, in Kensey, a special applicator is used. There, the applicator is inserted into a dedicated procedural sheath (other than the introducer used to position the catheter). An anchor member is placed on the tip of the applicator, and a collagen plug is secured within the applicator adjacent the tip. A filament traverses the length of the applicator and also connects the anchor member and the plug. The Kensey device provides advantages in that one sheath length fits all arterial depths, and a configuration is provided (e.g., the anchor member) to seek to position the collagen plug at the puncture site. However, in Kensey the anchor member remains in the arterial lumen after closure of the puncture is completed. Thus, a foreign object potentially impedes the natural flow of blood to the peripheral vasculature and could become dislodged. Also, as may be appreciated, the applicator with its spring-loaded arrangement is relatively complicated.

Other devices that use collagen plugs to effect closure of the puncture site are shown in U.S. Pat. No. 5,192,300, issued Mar. 9, 1993 to Fowler, "Insertion Assembly and Method of Inserting a Vessel Plug Into the Body of a Patient," and U.S. Pat. No. 5,522,840, issued Jun. 4, 1996 to Krajicek, "Device for the Non-Surgical Seal of the Interstice in the Wall of a Vessel," which are incorporated herein. The Fowler device requires use of a separate balloon catheter to locate the puncture site as well as a collagen applicator. The balloon catheter is inserted through the introducer catheter, the introducer catheter is removed, and then the collagen plug is inserted to the puncture site along the shaft of the balloon catheter. The balloon catheter is then removed such that the only means of retaining the plug at the puncture site is tissue at the puncture site surrounding the plug.

Gershony also utilized an inflated balloon to locate the puncture site, but it is a separate device (not a balloon catheter). Gershony relied on a subsequent injection of procoagulant substances through the introducer sheath, presenting the risk of pushing the liquid-like substances into the vasculature and producing an embolism. The Krajicek device comprises a particular type of collagen plug and an applicator that may be applied to the exterior of the introducer. The Krajicek device does not include a mechanism for locating the puncture site. Makower shows a device similar to Krajicek in that thrombogenic materials are disposed concentrically surrounding the introducer which are pushed down the length of the introducer to the puncture site. Like Janzen, Makower requires a measuring procedure before the start of the closure procedure, e.g., a sheath and dilator having graduated markings are used (col. 6, 1. 18–20).

As can be seen, many of these devices require use of additional, specialized applicators. These applicators present disadvantages in that, among other things, they impose further costs on the procedure and may lead to additional bleeding while the special applicator is positioned for deployment. These applicators, being separate devices, are expensive. An additional step must be performed, requiring more time and training of the health-care professionals, and in some cases the catheter and introducer must be removed, presenting the risk of bleeding. Also, some of the devices lack a means for locating the arterial puncture site. Where mechanisms are not provided for precisely locating the puncture site, there is a risk that thrombogenic materials will enter the lumen.

As may be appreciated, those involved in the field of medical devices, and particularly medical devices useful for vascular sealing, continue to seek to develop new designs to quickly seal puncture sites. In particular, it would be advantageous to have a device that can quickly and easily deliver thrombogenic materials to the puncture site exterior the artery. It also would be advantageous to provide a mechanism for delivering these materials to the puncture site without having to remove the original procedural introducer and without having to incur the expense and technical difficulties associated with additional applicator devices.

SUMMARY OF THE INVENTION

Summarily described, the invention embraces a surgical instrument adapted to be inserted through a puncture in a wall of a patient's blood vessel for use in placing a medical device into the lumen of the blood vessel. The instrument has a vascular sealing mechanism integrated thereon. The instrument includes an elongated introducer and a vessel-engaging component. The introducer has a substantially cylindrical wall with an inner bore, a proximal end, and a distal end. The distal end is configured to be inserted through the puncture into the lumen of the blood vessel. The inner bore is dimensioned to receive the medical device and opens at the distal end so that the medical device may protrude from the distal end into the lumen of the blood vessel when the distal end is inserted into the lumen. The wall has a channel therein that opens to the exterior surface at one point adjacent the distal end and at another point adjacent the proximal end to define a distal window and a proximal window, respectively.

The vessel-engaging component comprises an elongated filament engaged within the channel. The filament has a first end, a second end, and an expandable part or member at the second end that is changeable from a first configuration to at least a second, expanded configuration. The first end of the filament protrudes from the proximal window and is adjustable from a first state to at least a second state. The second end is disposed adjacent the distal window with the expandable member positioned at the distal window such that, when the first end is in the first state, the expandable member is seated substantially within the channel adjacent the distal window, and when the first end is adjusted from the first state to the at least second state, the expandable member is changed from the first configuration to the at least second configuration and is pushed out of the distal window. The diameter of the expandable member in the second configuration together with the diameter of the distal end of the introducer are adapted to be larger than the size of the puncture. Thus, when the distal end of the introducer is inserted into the lumen of the blood vessel and the member expanded, pulling the introducer through the puncture in a direction opposite the vessel causes the expandable member to be engaged on the vessel wall at the location of the puncture to provide resistance. In this way, the vessel-engaging component is adapted to locate the puncture site. Advantageously, the instrument further has a sealing component comprising an applicator and a plurality of rings on the wall of the introducer. The rings may be tapered and are fabricated with one or more different types of materials or mixtures thereof, e.g., including antibiotics, pain killers, and procoagulants.

BRIEF DESCRIPTION OF THE DRAWINGS

For a better understanding of the invention, an exemplary embodiment is described below, considered together with the accompanying drawings, in which:

FIG. 2A shows a side view of one embodiment of the inventive introducer with the vessel-engaging component in its undeployed "at rest" position;

FIG. 2B shows the view of FIG. 2A with the vessel-engaging component in its deployed position;

FIG. 7A shows an exploded cut-away view of an alternative embodiment of the introducer showing the distal and proximal regions of the introducer in the undeployed state; and FIG. 7B shows the view of FIG. 7A in the deployed state.

It is to be understood that these drawings are for the purposes of illustrating the concepts of the invention and are not to scale. Like character references are used to refer to like elements of the invention throughout the drawings.

DETAILED DESCRIPTION OF THE INVENTION

Figure 1:
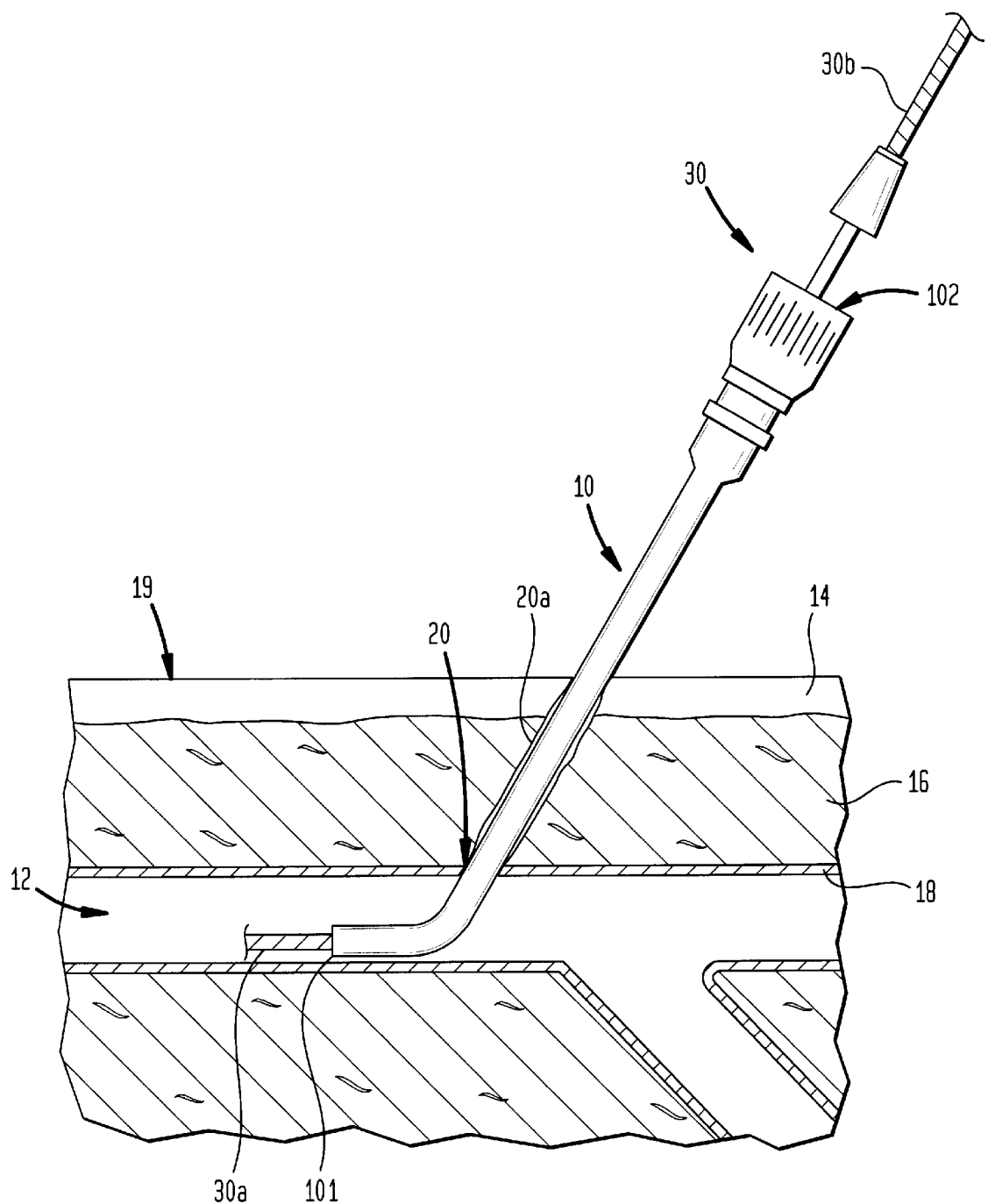
FIG. 1 shows a schematic cross-sectional view of a patient's artery with a typical introducer and catheter inserted therein.

With this invention, an introducer is provided having an integral vascular sealing mechanism. The integral sealing mechanism essentially has two parts. The first part comprises a vessel-engaging component, preferably a filament with an expandable part, the filament being releasably attached to or engaged on or in the wall of the introducer. By "expandable" it is meant that the member is adjustable from a small-diameter state to a larger-diameter state. The vessel-engaging component aids in locating the site of the puncture. The second part comprises a sealing component for effecting closure of the puncture once it has been properly located. By providing a mechanism on the introducer itself that both locates and effects closure of the puncture, the invention enables a simpler procedure, avoids costs associated with additional applicators, and reduces bleeding associated with unnecessary transfers of devices into and out of the artery.

More particularly with reference to the figures, FIG. 2A shows a side view of one embodiment of the inventive introducer 40 with the vessel-engaging component 45 in its undeployed "at rest" position. FIG. 2B shows the view of FIG. 2A with the vessel-engaging component in its deployed position. The introducer with the integral locating and sealing mechanism in combination are generally referred to herein as a "surgical instrument." The instrument is adapted to be inserted through a puncture in a wall of a patient's blood vessel for use in placing a medical device, e.g., a catheter, into the lumen of the blood vessel. The process of inserting the introducer into the blood vessel is described in further detail below with reference to FIGS. 4A–4E. Although the introducer and the process of using it are described below with reference to an artery, it should be understood that the introducer may be used with any blood vessel including any vein or artery.

Looking at FIGS. 2A–3B, the surgical instrument comprises an elongated introducer 40 having a substantially cylindrical wall 46, with an exterior surface 41 and an interior surface 43 (represented with hatched lines in FIGS. 2A–2B). FIG. 3A shows a cross-sectional view of the embodiment of FIGS. 2A–2B taken along the line 3—3 of FIG. 2A, with the wall clearly depicted in FIG. 3A. As shown in FIG. 2A, the introducer has a proximal end 40a and a distal end 40b. The distal end 40b is configured to be inserted through the puncture into the arterial lumen (as described further below). The interior surface defines an inner bore 44 traversing the length of the introducer, e.g., opening at the proximal end 44a and at the distal end 44b (FIG. 2B). The inner bore is dimensioned to receive the medical device (e.g., the catheter), so that the medical device may protrude from the distal end into the arterial lumen when the distal end is inserted into the lumen. The wall of the introducer has at least one elongated channel 48 therein (FIG. 3A), and it may have a plurality of channels. The wall of the introducer may be wider in the region adjacent the channels to provide structural support. In FIGS. 2A–2B, the inner channel of the introducer 40 is occupied by the vessel-engaging component 45 and is therefore not shown. The channel opens to the exterior surface at one point adjacent the proximal end 42a and at another point adjacent the distal end 42b to define a proximal window 42a and a distal window 42b, respectively.

The vessel-engaging component of this invention includes an elongated filament 45 having an expandable part or member 45b disposed or integrally formed thereon. The filament 45 is engaged within the channel 48, and it has a first end 45a and a second end 45b. As can be seen from FIG. 3A, the filament 45 may be fully embedded within a wall 46 of the introducer. In that case, the filament will be covered by the exterior surface, i.e., not exposed to the ambient, except at the proximal and distal windows. In an alternative embodiment, the channel may be dimensioned in the shape of a groove or slit, such that all or a portion of the length of the filament is exposed to the ambient. In any case, the filament advantageously is engaged on or in the wall along its length so that the one end is accessible at the proximal end of the introducer and the other end is disposed at the distal end of the introducer with an expandable part seated thereon.

As seen in FIG. 2A, the first end 45a protrudes from the proximal window 42a beyond the exterior surface 41. In the embodiment shown in FIGS. 2A–2B, the elongated filament comprises a metal wire slidably engaged within the channel. The wire has one end portion 45a protruding from the proximal window and another end section 45b positioned adjacent the distal window. Preferably, the wire is fabricated from stainless steel, nitinol, or another superelastic material having memory retention. As can be seen in comparing FIGS. 2A and 2B, the portion 45a of the filament is adjustable from a first state to at least a second state. In the embodiment of FIGS. 2A–2B, the first state comprises the portion 45a of the wire being in an extended or stretched position outside the exterior surface of the wall (FIG. 2A), and the second state comprises the portion 45a of the wire being pushed into the proximal window (FIG. 2B), following the arrow "p" of FIG. 2A. The converse may also apply. For example, as described below with reference to FIGS. 7A and 7B, the first state may comprises the portion 45a of the wire being pushed into the proximal window (FIG. 7A), with the second state comprising the portion 45a being in an extended or stretched position outside the exterior surface of the wall (FIG. 7B).

In FIGS. 2A–2B, the expandable member comprises a section 45b of the wire. The member 45b is disposed adjacent the distal window 42b. In the embodiment of FIGS. 2A–2B, the tip 45c of the filament is anchored into the distal end 40b of the introducer, and the expandable member comprises a section of the wire popping out of the distal window in a looped configuration 45b (FIG. 2B). In an alternative embodiment (e.g., FIG. 6), the very tip 45c of the filament itself protrudes from the distal window 42b. In any case, when the portion 45a of the wire is pulled out of the proximal window, as in FIG. 2A, the member 45b is seated substantially within the channel adjacent the distal window. However, when the portion 45a is pushed into the channel, following the arrow "p" of FIG. 2A, the member 45b at the distal end is pushed out of the distal window 42b. The composition of the filament is such that the end section 45b buckles, coils, bends, twists, loops, or otherwise deforms into an expanded second configuration, as shown in FIG. 2B. Any configuration may be used, provided the diameter of the filament in this second configuration 45b together with the diameter of the distal end of the introducer are adapted to be larger than the size of the puncture. This expanded configuration enables the practitioner to locate the puncture site as resistance is provided at the site when the distal end of the introducer is pulled in a direction out of the artery. A small loop or handle 47 (FIG. 2B), may be disposed at the proximal portion of the wire to aid in pushing or pulling the wire into a deployed or undeployed state.

Figure 3A:
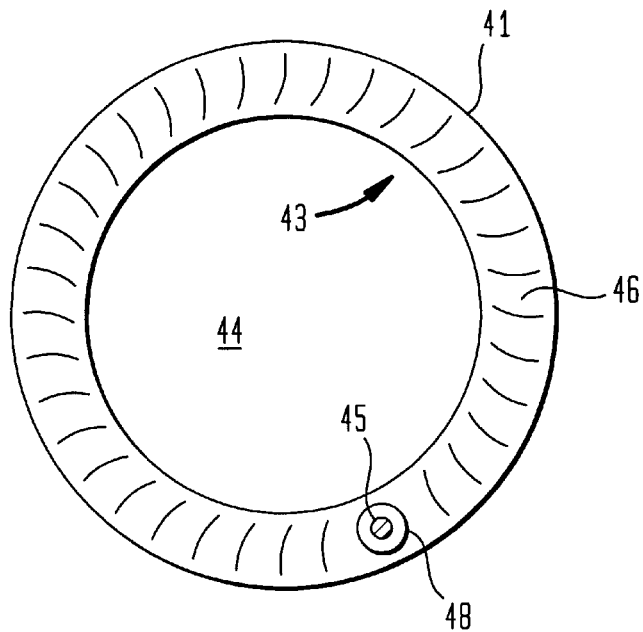
FIG. 3A shows a cross-sectional view of the embodiment of FIGS. 2A taken along the line 3—3 of FIG. 2A.
Figure 3B:
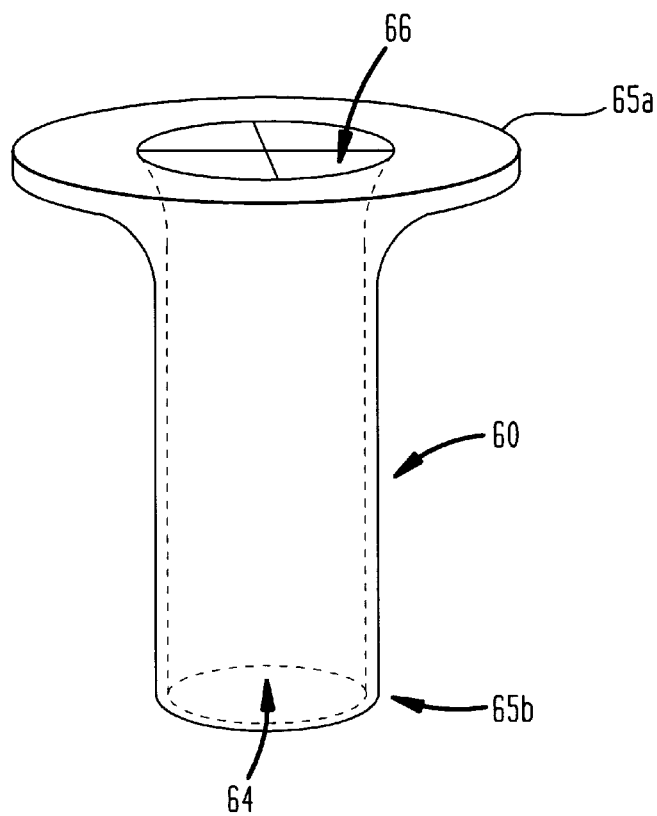
FIG. 3B shows a perspective view of the applicator of FIGS. 2A–2B.

FIG. 3B shows a perspective view of an applicator 60 that comprises part of the sealing mechanism. Once the puncture site has been located, e.g., using the vessel-engaging component described above, the sealing mechanism may be applied to effect closure of the puncture. The sealing mechanism comprises the applicator 60 and a plurality of thrombogenic rings 62a . . . 62e (FIG. 2B), suspended on the exterior surface 41 of the introducer. The thrombogenic material is biocompatible and bioresorbable and may comprise collagen, thrombin, or mixtures thereof The applicator 60 may take many forms but preferably is configured as in FIG. 3B, comprising a plug having a hole 64 traversing its length from a proximal end 65a to a distal end 65b. The hole 64 is dimensioned so that the applicator 60 may be suspended and slid along the exterior surface 41 of the introducer. Thus, the diameter of the applicator hole 64 should be slightly larger than the diameter of the introducer exterior. A hemostatic valve 66 advantageously is disposed over the opening of the applicator at the proximal end, to prevent the emission of blood or other fluids, as is known in the field.

The plurality of rings are disposed between the applicator 60 and the distal end 40b of the introducer. In this way, when the applicator is pushed toward the distal end, the applicator also pushes the thrombogenic rings toward the distal end, where the expandable member 45b is also located. If the expandable member has been lodged against the puncture, the practitioner can be assured that pushing the thrombogenic material toward the distal end will have the effect of placing that material at the puncture site to effect closure. Before the applicator 60 and rings 62a–62e are engaged, a disposable and removable plastic piece or wrap 70 may be applied to surround them (FIG. 2A), so that the rings are secured in place while the instrument is being used to position the catheter (30, FIG. 1), into the arterial lumen. The plastic piece 70 also may be applied over and retain the proximal portion 45a of the wire onto the introducer during the procedures to protect against the expandable member inadvertently engaging or the rings being prematurely affected by blood or contaminants.

Advantageously, about two to twenty rings may be used. Each ring may have an outer radius of about 3 to 15 mm, an inner radius of 2–10 mm, and a thickness (or length) ranging from 0.1 to 3 mm. The first several (e.g., 1 to 3) rings nearest the distal end of the introducer may be tapered and denser than the other rings to facilitate entry into the wound tract. Some or all of the rings may be comprised of a mixture of materials, e.g., in addition to thrombogenic materials, heparin-inactivating agents, antibiotic or antimicrobial compositions or pain killers may be used to fabricate one or more of the rings. In this way, multifunctional applications can be allocated to different rings depending on their position relative to the puncture site. For example, rings located nearest the puncture site, e.g., near the distal end of the introducer, will reach the puncture site first and therefore advantageously may contain primarily procoagulants. Rings located closer to the proximal end of the introducer advantageously contain antibiotic or anti-microbial compositions or pain killers, such as analgesics or anesthetics.

Use of the plurality of rings provides many advantages, besides allowing for multi-functional applications. Tapering the rings and varying their size not only facilitates their application to the puncture site but also allows for conformability to the contours of the wound tract, that is, differently sized and shaped rings may be used so that they will conform to the dimensions of the wound tract 20a. As compared with a single thrombogenic plug, the rings provides advantages in terms of transmitting stresses and avoiding buckling. Use of a plurality of rings further allows for easy adjustment of the instrument to patient demands, i.e., for larger patients, more or larger rings may be placed on the introducer. The same introducer device thus may be used for different patients despite their differing levels of subcutaneous fat. It is known by those skilled in the art that the swelling of the rings can be controlled by various means. The rings will swell to further aid in sealing the puncture.

Looking back to FIG. 2B, a marker 49 may be placed on the exterior of the introducer at a distance $d_1$ from the distal window 42b. The distance $d_1$ advantageously is approximately equal to the distance $d_2$, where $d_2$ reflects the combined length of the applicator and the rings, e.g., the length from the most distal located ring 62e to the proximal end of the applicator 65a. The marker assists in properly positioning the rings at the puncture site. In operation, when the practitioner pushes the applicator so that its proximal end 65a is lined up with the marker 49, the practitioner can be assured that the most distal located ring 62e will be positioned adjacent the distal window 42b of the introducer and thus, at the puncture site.

Figure 4A:
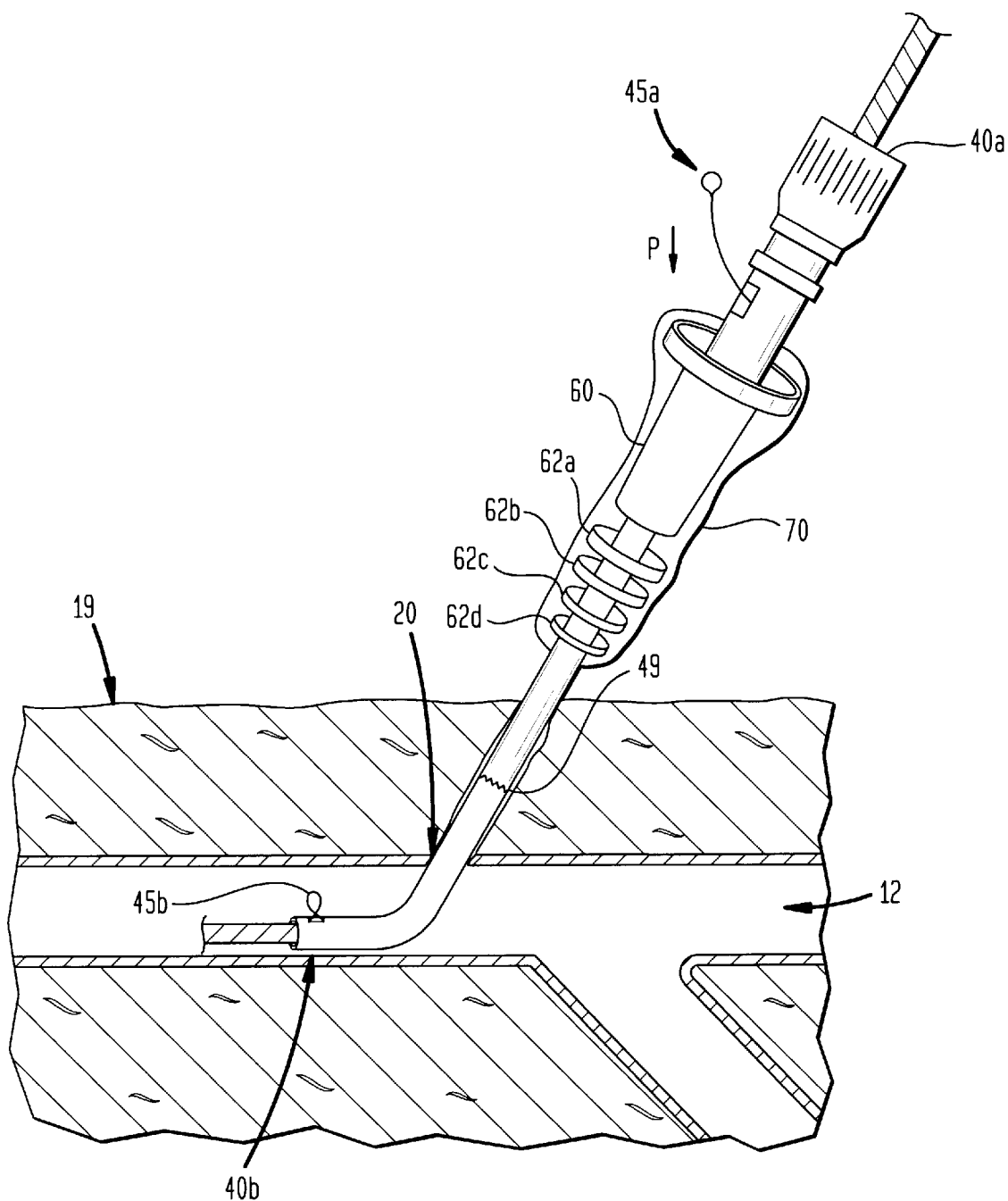
FIGS. 4A–4F show the embodiment of FIGS. 2A–2B in use in effecting closure of an arterial puncture site.

FIGS. 4A–4F illustrate the operation of the locating and sealing mechanism of the inventive introducer. The vessel-engaging component including the elongated filament and expandable member are adapted for use in determining the location of the puncture, and then the sealing mechanism is applied to effect closure of the puncture. In FIG. 4A, the distal end 40b of the introducer has been inserted into the lumen of an artery or other vessel 12. In this view, the catheter 30 is retained in the introducer. Alternatively, the catheter may be removed.

In FIG. 4A, the proximal end of the introducer 40a and the proximal portion of the filament 45a protrude beyond the exterior surface of the patient's skin 19. In this way, the proximal portion 45a of the filament may be adjusted from the first state to the at least second state to push the expandable member 45b into the vessel lumen and change the member from the first configuration to a second expanded configuration. In FIG. 4A, this is accomplished by pushing the portion of the wire at 45a into the introducer, e.g., following arrow "p," such that the distal end section 45b of the wire deforms into a looped configuration. The applicator 60 and plurality of thrombogenic rings are secured in a plastic wrap 70 along the length of the introducer, and they also are located beyond the patient's skin 19.

Figure 4B:
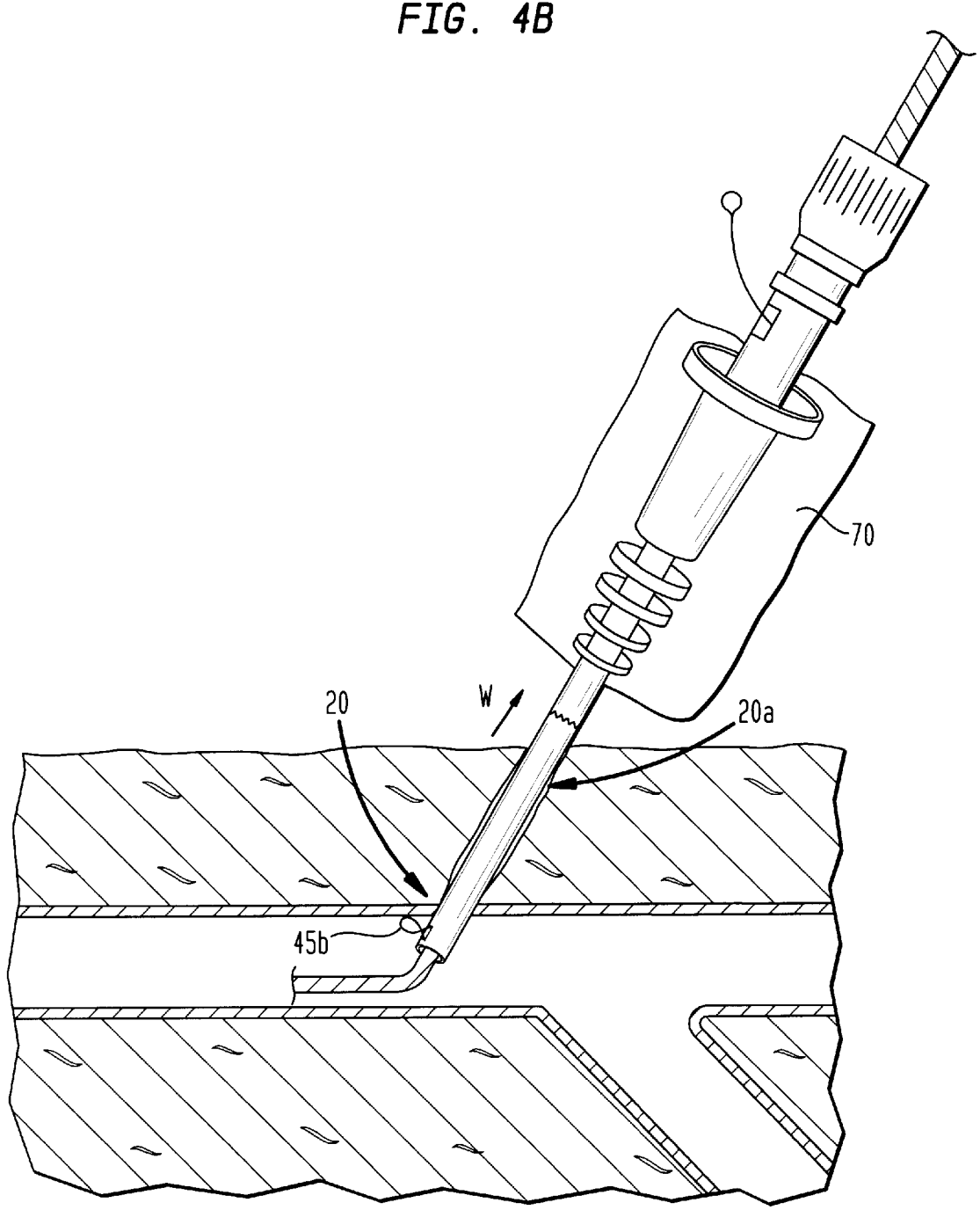

Looking at FIG. 4B, once the member 45b is expanded, the introducer is partially withdrawn from the patient's skin, through the puncture 20 and wound tract 20a, in a direction opposite the artery, e.g., following arrow "w". Due to the large diameter of the member 45b, the vessel-engaging component engages on the arterial wall at the location of the puncture to provide resistance in pulling the introducer away from the artery. This resistance assures the practitioner that the puncture site has been found. Although FIG. 4B shows one member 45b engaged on the arterial wall, more than one expandable member may be incorporated into the introducer to provide additional resistance and further assurance that the practitioner has located the puncture site. Once the site is located, the plastic wrap 70 may be removed so that the sealing mechanism can be applied.

Figure 4C:
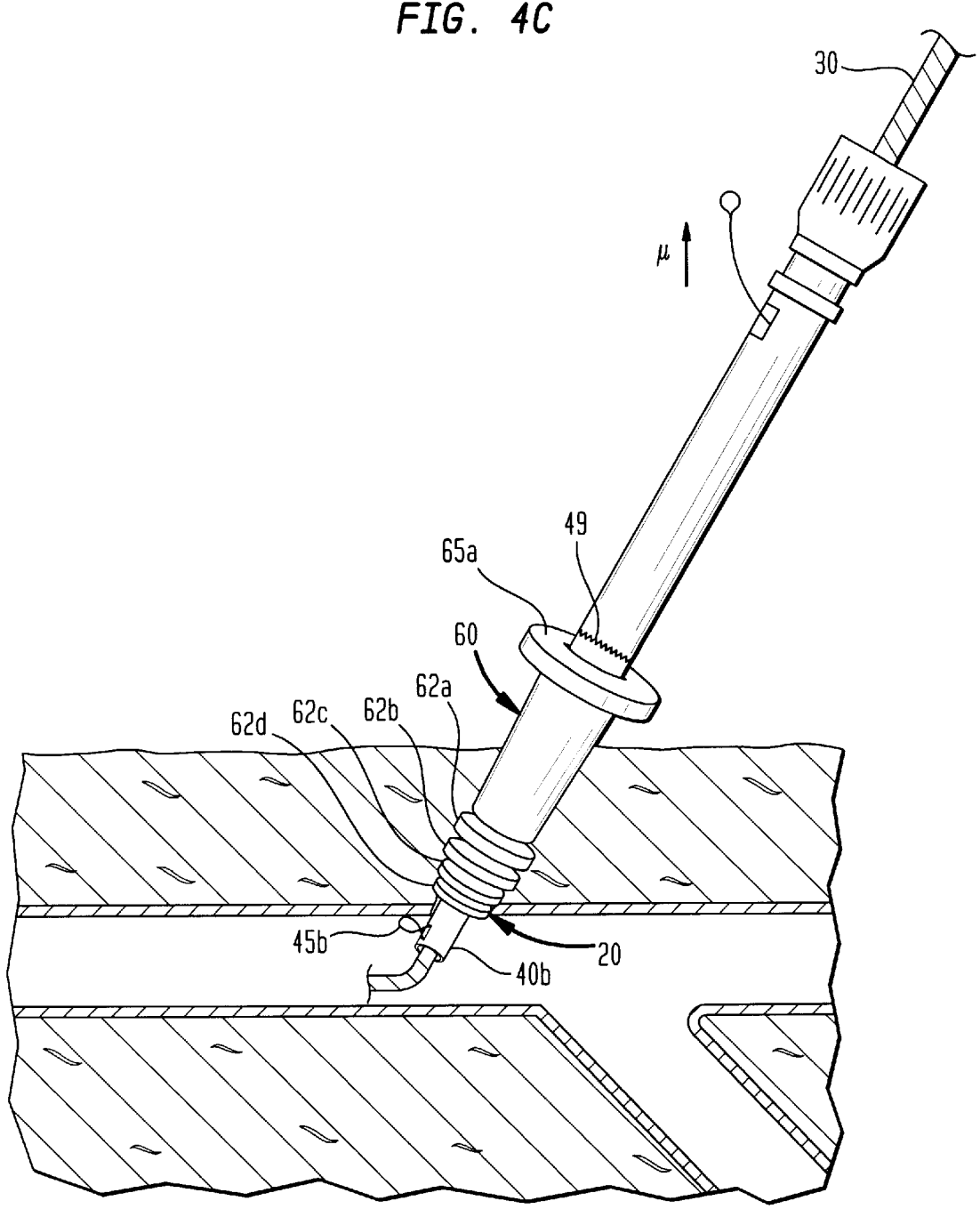

Looking at FIG. 4C, the sealing mechanism is shown. The applicator 60 is pushed downward along the length of the introducer to push the rings 62a, 62b, 62c, 62d, to the puncture site 20. The applicator 60 is moved so that its proximal end 65a is adjacent the marker 49. Since the distance from the distal window 42b of the introducer to the marker 49 is substantially the same as the combined length of the applicator and the rings, the practitioner is assured that the rings are placed adjacent the distal window 42b, and thus, at the puncture site 20. Once the rings are positioned, the filament may be pulled upward, e.g., following arrow "u," to return the expandable member 45b to its first, undeployed state (as in FIG. 2A).

Figure 4D:
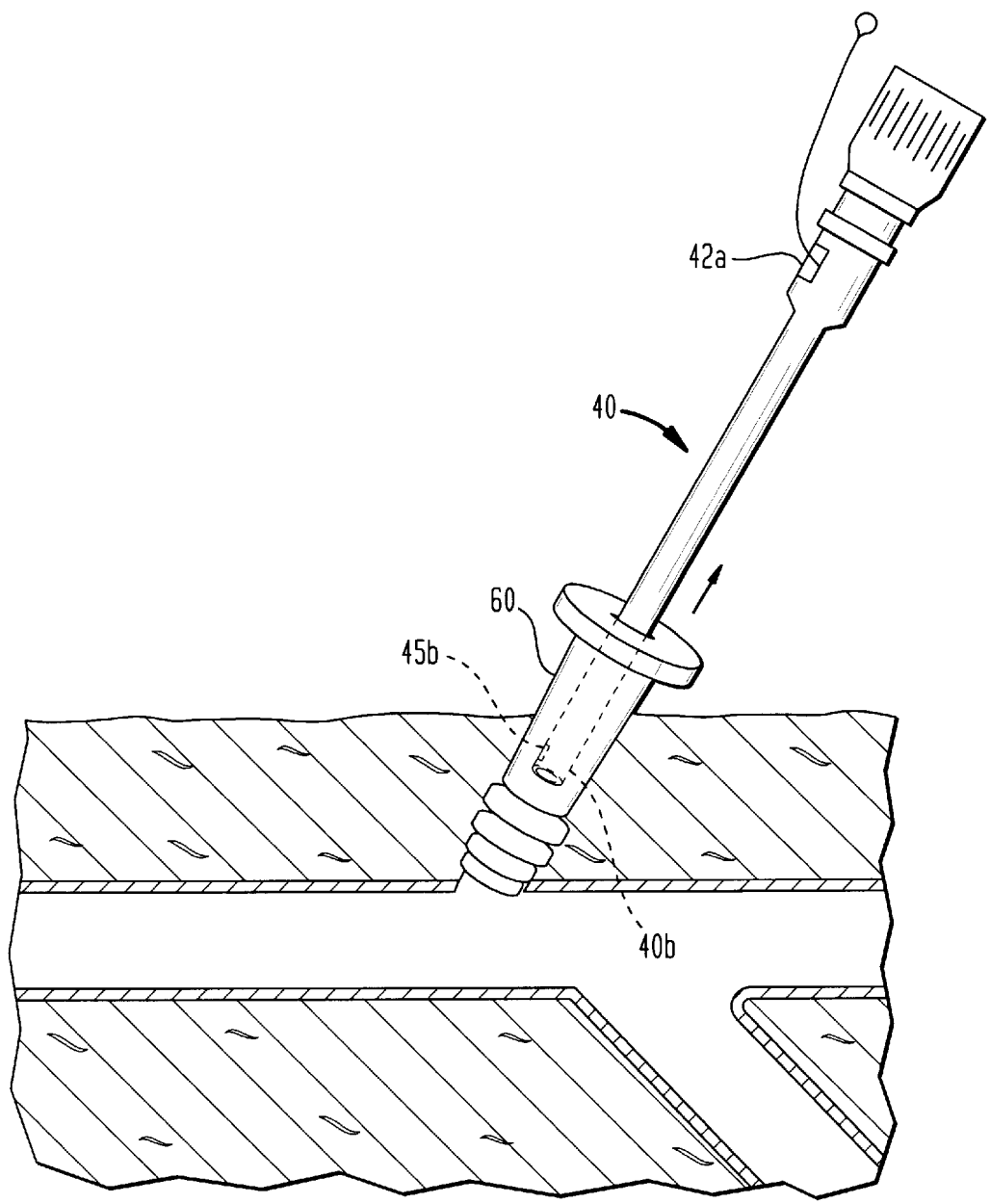
Figure 4E:
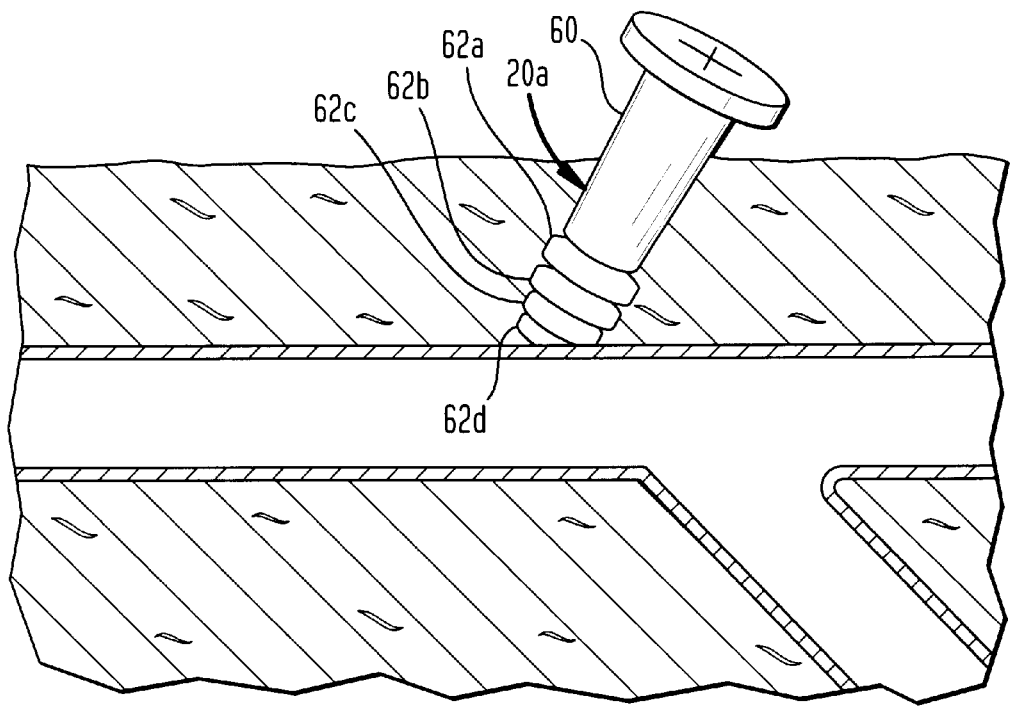
Figure 4F:
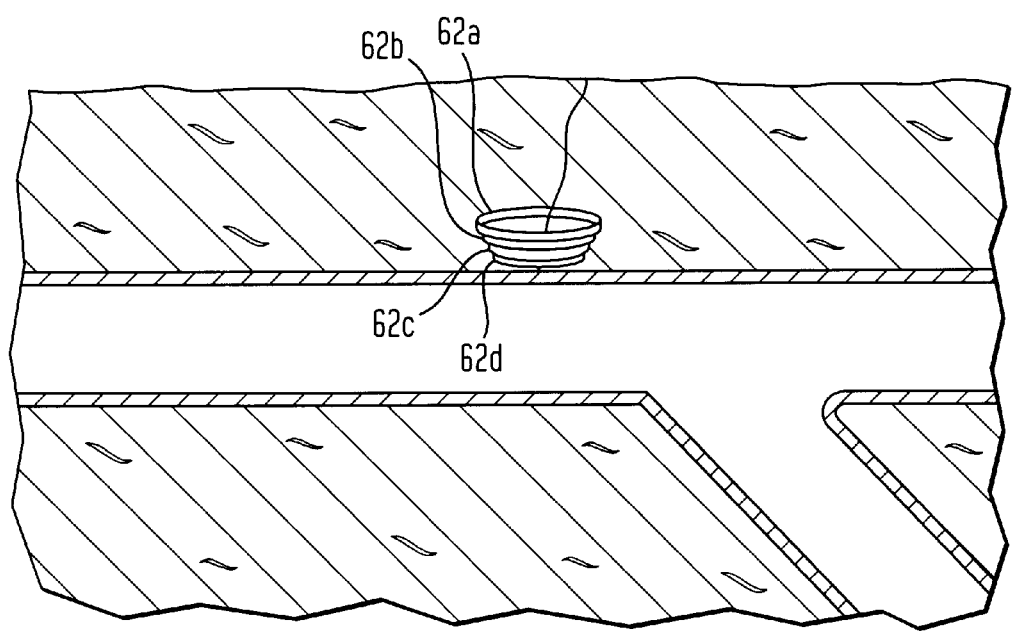

Looking at FIG. 4D,. once the thrombogenic rings have been positioned and the expandable member returned to the undeployed state, the catheter 30 and introducer 40 may be removed. In the view of FIG. 4D, the catheter 30 has been fully removed, and the introducer is in the process of being pulled upward from the applicator 60, with the distal end 40b of the introducer still within the applicator and shown with hatched lines. The proximal portion of the filament 45a has been pulled out of the proximal window 42a so that the expandable member has been returned to its first, non-expanded configuration 45b. This enables the practitioner to retrieve the instrument from the puncture site 20 and the applicator, as shown. Next, in FIG. 4E, the introducer 40 has been filly removed and only the applicator 60 and rings 62a–62d remain in the wound tract 20a. The applicator and rings may be left in the wound tract until hemostasis is achieved. The applicator is then removed, as shown in FIG. 4F, leaving only the rings remaining at the puncture site 20.

Figure 5:
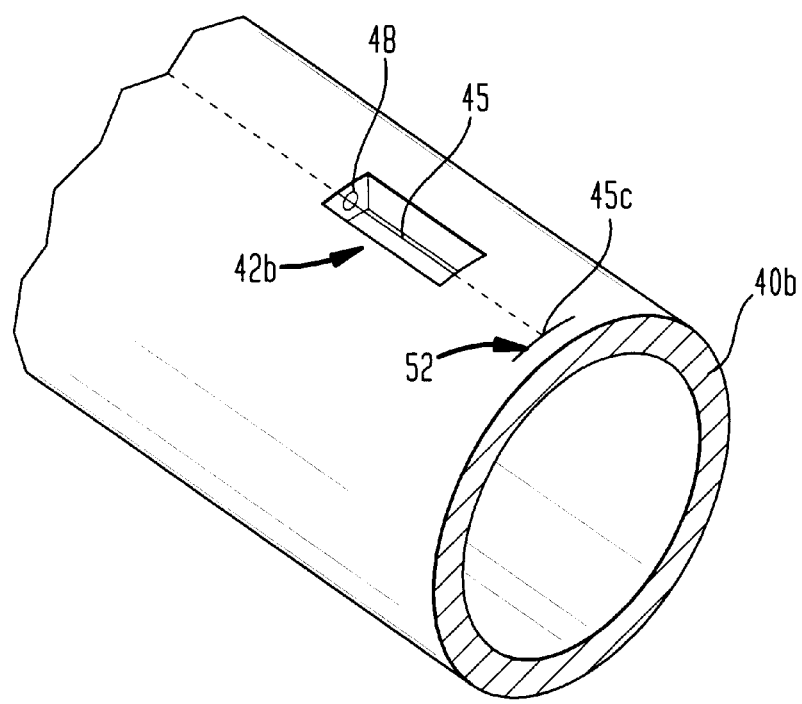
FIG. 5 shows an exploded perspective view of the distal end of the introducer at boxed region 6—6 of FIG. 2B.
Figure 6:
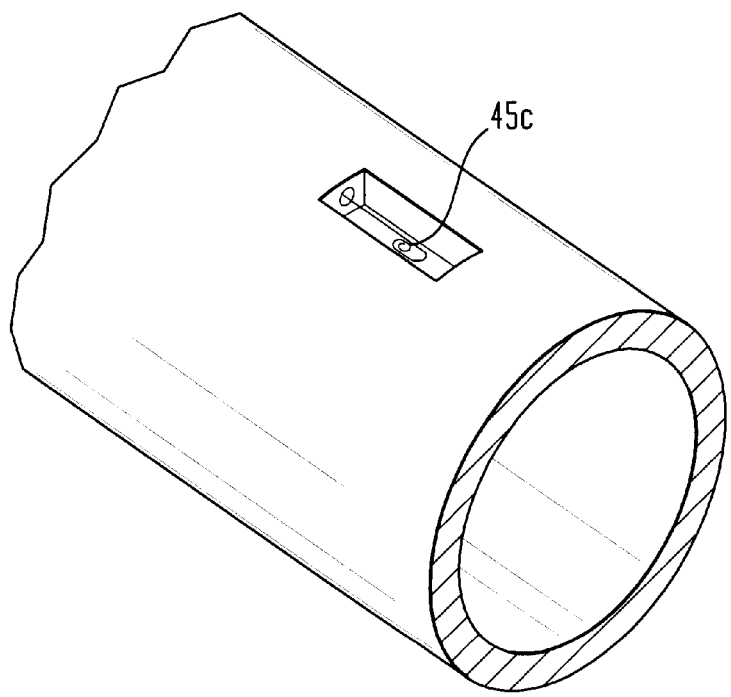
FIG. 6 shows an exploded perspective view of the distal end of an alternative embodiment of the inventive introducer.

FIGS. 5 and 6 show exploded perspective views of the introducer tip, with FIG. 5 showing the embodiment of FIG. 2B at boxed region 5—5 of FIG. 2B and FIG. 6 showing an alternative embodiment. In FIG. 5, the tip of the wire 45c is attached to an anchor 52 at the distal end of the introducer. The anchor 52 may take many configurations, such as a bar (as shown) or beads. It secures the filament within the channel and prevents the wire from piercing the introducer and protruding from the distal end when the filament is pushed within the channel 48. When the proximal portion 45a of the filament is pushed into the proximal window 42a (FIG. 2B), the end section 45b of the wire at the distal end pops out of the distal window 42b. In FIG. 6, the tip 45c of the filament is a free end that may curl into a coiled configuration when the filament is pushed. The wire may have a circular shape, or it may be flat, e.g., as with a ribbon.

FIGS. 7A and 7B show yet another embodiment of the introducer, with FIG. 7A showing an undeployed state and FIG. 7B showing a deployed state. In these figures, a cut-away view is provided (the midsection of the introducer is cut-away) so that the proximal window 42a and distal window 42b can be seen together in exploded views. Here, the tip 45c of the filament 45 is not anchored in the introducer but may slide within the channel 48 (shown with hatched lines), up to a point 59. A certain length 55 of the filament between the distal end 40b and the distal window 42b is afforded with a shaped-memory effect so that it will deform into a coiled or other twisted or bent configuration when not constrained within the channel 48. In FIG. 7A, the proximal portion 45a of the filament is pushed into the proximal window 42a so that the shaped length 55 of the filament is constrained within the channel. In FIG. 7B, the portion 45a is pulled from the distal window, and the tip 45c of the filament then slides within channel 48 toward the distal window 42b. When the end 45c of the filament reaches the point 59, the length 55 having the shaped memory pops out of the window in a coiled or twisted configuration.

In another embodiment, the expandable member may include a small balloon (not shown) that may be inflated to have an expanded diameter and protrude from the distal window. In that case, an inflation bulb may be provided at handle 47, and the filament 45 may be hollow for use in inflating the balloon.

Although the instrument is shown here with only one channel, one expandable member, and one filament, a plurality of such components may be placed on the introducer, for example, on either side. In this way, greater resistance may be provided when the introducer is pulled from the puncture site, further increasing the likelihood that the puncture site has been properly located. The introducer itself may be fabricated from materials known to those skilled in the field for making procedural sheaths, e.g., various biocompatible polymers are known. The design of the introducer adjacent the proximal end 40a also may follow designs known in the field, for example, side-arm extensions and the like may be used.

It is understood that the embodiments described herein are merely exemplary and that a person skilled in the art may make variations and modifications without departing from the spirit and scope of the invention. All such variations and modifications are intended to be included within the scope of the appended claims.

I claim:

1. A surgical instrument adapted to be inserted through a puncture in a wall of a patient's blood vessel for use in placing a medical device into the lumen of the blood vessel, the instrument comprising:

(a) an elongated introducer having a substantially cylindrical wall with an exterior surface and an interior surface, the interior surface defining an inner bore traversing the length of the introducer, in which (i) the introducer has a proximal end and a distal end with the distal end configured to be inserted through the puncture into the vascular lumen, (ii) the inner bore is dimensioned to receive the medical device and opens at the distal end so that the medical device may protrude from the distal end into the vascular lumen when the distal end is inserted into the vascular lumen, and (iii) the wall has a channel therein that opens to the exterior surface at one point adjacent the distal end and at another point adjacent the proximal end to define a distal window and a proximal window, respectively; and (b) a vessel-engaging component comprising an elongated filament engaged in the channel having a first end, a second end, and an expandable part at the second end changeable from a first configuration to at least a second, expanded configuration, in which (i) the first end protrudes from the proximal window beyond the exterior surface and is adjustable from a first state to at least a second state, and (ii) the second end is disposed adjacent the distal window with the expandable part positioned at the distal window such that, when the first end is in the first state, the expandable part is seated substantially within the channel adjacent the distal window, and when the first end is adjusted from the first state to the at least second state, the expandable part is changed from the first configuration to the at least second configuration and is pushed out of the distal window, whereby the diameter of the expandable part in the second configuration together with the diameter of the distal end of the introducer are adapted to be larger than the size of the puncture, whereby the vessel-engaging component is adapted for use in determining the location of the puncture in that, when the distal end of the introducer is inserted into the vascular lumen, the proximal end of the introducer and the first end of the filament protrude beyond the patient's skin such that the first end of the filament may be adjusted from the first state to the at least second state to change the expandable part from the first configuration to the at least second expanded configuration, such that pulling the introducer in a direction opposite the blood vessel causes the expandable part to be engaged on the vascular wall at the location of the puncture to provide resistance in pulling the introducer away from the blood vessel.

2. The instrument of claim 1, further comprising (i) an applicator with a hemostasis valve adapted to be disposed on the exterior surface of the wall, and (ii) a plurality of rings suspended on the exterior surface of the wall, the plurality of rings being fabricated from at least one of a thrombogenic material, a pain killer, and an antibiotic or anti-microbial composition, wherein the plurality of rings are disposed between the applicator and the distal end so that when the applicator is pushed toward the distal end, the applicator pushes the plurality of rings toward the distal end.

3. The instrument of claim 2, in which the exterior surface of at least one of the plurality of rings is tapered to facilitate access to the puncture site.

4. The instrument of claim 2, further comprising a removable plastic member or covering the applicator and the plurality of rings prior to use.

5. The instrument of claim 2, further comprising a marker disposed on the exterior wall of the introducer, in which the distance between the proximal edge of the distal window of the introducer and the marker is substantially the same as the combined length of the applicator and the plurality of rings.

6. The instrument of claim 2, in which each of the plurality of rings has an inner radius of about 2 to 10 mm, an outer radius of about 3 to 15 mm and a thickness of from about 0.1 to 3 mm.

7. The instrument of claim 1, in which elongated filament comprises a metal wire slidably engaged within the channel and the expandable part comprises a section of the wire.

8. The instrument of claim 7, in which the wire is fabricated from stainless steel or a superelastic material with memory retention.

9. The instrument of claim 8, in which the superelastic material is nitinol.

10. The instrument of claim 7, in which the first configuration comprises the end section of the wire lying substantially flat within the channel and the second configuration comprises the section of the wire protruding from the distal window and being deformed into a configuration selected from looped, twisted, bent, buckled, or coiled shapes.

11. The instrument of claim 7, in which the first state comprises a portion of the wire being in an extended position outside the proximal window and the second state comprises the portion of the wire being pushed into the proximal window.

12. The instrument of claim 7, in which the first state comprises the portion of the wire being pushed into the proximal window and the second state comprises a portion of the wire being in an extended position outside the proximal window.

13. A surgical instrument adapted to be inserted through a puncture in a wall of a patient's blood vessel for use in placing a medical device into the lumen of the blood vessel, the instrument comprising:

(a) an elongated introducer having a substantially cylindrical wall with an exterior surface and an interior surface, the interior surface defining an inner bore traversing the length of the introducer, in which (i) the introducer has a proximal end and a distal end with the distal end configured to be inserted through the puncture into the vascular lumen, (ii) the inner bore is dimensioned to receive the medical device and opens at the distal end so that the medical device may protrude from the distal end into the lumen when the distal end is inserted into the lumen, and (iii) the wall has a channel therein that opens to the exterior surface at one point adjacent the distal end and at another point adjacent the proximal end to define a distal window and a proximal window, respectively; and (b) a vessel-engaging component comprising an elongated filament slidably engaged within the channel having a first end, a second end, and an expandable part at the second end, in which (i) the first end protrudes from the proximal window beyond the exterior surface and may be pulled out from or pushed toward the proximal window, and (ii) the second end is disposed adjacent the distal window with the expandable part positioned at the distal window such that, when the first end is pulled out from the proximal window, the expandable part is seated substantially within the channel adjacent the distal window, and when the first end is pushed toward the proximal window, the expandable part pops out of the distal window and changes into a deformed configuration, whereby the diameter of the expandable part in the deformed configuration together with the diameter of the distal end of the introducer are adapted to be larger than the size of the puncture, whereby the vessel-engaging component is adapted for use in determining the location of the puncture in that, when the distal end of the introducer is inserted into the lumen, the expandable part may be changed to its deformed configuration, such that pulling the introducer in a direction opposite the blood vessel causes the expandable part to be engaged on the vascular wall at the location of the puncture to provide resistance in pulling the introducer away from the blood vessel; and (c) a sealing component comprising an applicator with a hemostasis valve and a plurality of rings, the applicator and plurality of rings being suspended on the exterior surface of the wall, wherein the plurality of rings are fabricated from at least one of a thrombogenic material, a heparin-inactivating agent, a pain killer, and an antibiotic or antimicrobial composition and are disposed between the applicator and the distal end so that when the applicator is pushed toward the distal end, the applicator pushes the plurality of rings toward the distal end.

14. The surgical instrument of claim 13, in which the deformed configuration is selected from looped, twisted, bent, buckled, or coiled shapes.

15. The surgical instrument of claim 13, in which the wall has two channels, one on either side of the elongated introducer, and a vessel-engaging component is disposed within each one of the two channels.

16. The surgical instrument of claim 13, in which the thrombogenic material is selected from collagen or thrombin, the heparin-inactivating agent is protamine, and the pain killer is at least one of an anesthetic or analgesic.

* * * * *